United States Patent [19]

Mahood

[11] Patent Number: 5,623,009

[45] Date of Patent: *Apr. 22, 1997

[54] NEO-DIOL PHOSPHITES AS POLYMER STABILIZERS

[75] Inventor: James A. Mahood, Parkersburgh, W. Va.

[73] Assignee: General Electric Company, Pittsfield, Mass.

[ * ] Notice: The term of this patent shall not extend beyond the expiration date of Pat. No. 5,424,348.

[21] Appl. No.: 415,394

[22] Filed: Apr. 3, 1995

Related U.S. Application Data

[63] Continuation of Ser. No. 307,545, Sep. 16, 1994, Pat. No. 5,424,348, which is a continuation of Ser. No. 96,530, Jul. 22, 1993, abandoned.

[51] Int. Cl.$^6$ .............................. C08K 5/527; C07F 9/02
[52] U.S. Cl. .............................................. 524/117; 558/85
[58] Field of Search ................................ 524/117; 558/85

[56] References Cited

U.S. PATENT DOCUMENTS

| | | |
|---|---|---|
| 3,039,993 | 6/1962 | Friedman . |
| 3,056,823 | 10/1962 | Hechenbleikner et al. . |
| 3,264,247 | 8/1966 | Friedman . |
| 3,281,381 | 10/1966 | Hechenbleikner et al. . |
| 3,305,520 | 2/1967 | Fritz et al. . |
| 3,305,526 | 2/1967 | Guttag . |
| 3,342,767 | 9/1967 | Buckley . |
| 3,415,906 | 12/1968 | Shepard et al. . |
| 3,437,720 | 4/1969 | Guttag . |
| 3,441,633 | 4/1969 | Friedman . |
| 3,467,733 | 9/1969 | Dever et al. . |
| 3,482,002 | 12/1969 | Dever et al. . |
| 3,483,147 | 12/1969 | Friedman . |
| 3,488,407 | 1/1970 | Schall . |
| 3,509,091 | 4/1970 | Cleveland et al. . |
| 3,558,554 | 1/1971 | Kuriyama et al. . |
| 3,646,173 | 2/1972 | Gordon et al. . |
| 3,714,302 | 1/1973 | Dever et al. . |
| 3,794,629 | 2/1974 | Eimers et al. . |
| 3,845,168 | 10/1974 | Guttag . |
| 4,086,304 | 4/1978 | Hutton et al. . |
| 4,196,117 | 4/1980 | Spivack . |
| 4,318,845 | 3/1982 | Spivack et al. . |
| 4,405,739 | 9/1983 | Kinson . |
| 4,529,533 | 7/1985 | Chasar . |
| 4,708,979 | 11/1987 | Pedrazzetti et al. . |
| 4,755,546 | 7/1988 | Hechenbleikner et al. . |
| 4,782,170 | 11/1988 | Bae et al. . |
| 4,882,374 | 11/1989 | Wang et al. . |
| 4,956,406 | 9/1990 | Myers et al. . |
| 4,957,954 | 9/1990 | Iizuka et al. . |

FOREIGN PATENT DOCUMENTS

| | | |
|---|---|---|
| 0392392A1 | 10/1990 | European Pat. Off. . |
| 0400454A2 | 12/1990 | European Pat. Off. . |
| 0576833A2 | 1/1994 | European Pat. Off. . |
| 0635514A1 | 1/1995 | European Pat. Off. . |
| 2944254 | 5/1980 | Germany . |
| 2087399 | 5/1982 | United Kingdom . |

OTHER PUBLICATIONS

*Phosphorus and Sulfur*, 1983, vol. 15, pp. 9–13.

Primary Examiner—Veronica P. Hoke

[57] ABSTRACT

A phosphite is provided having the formula:

$$H_3C-CH_2-CH_2-CH_2 \diagdown \diagup CH_2-O \diagdown$$
$$C \qquad P-O-\!\!\!\!\bigcirc\!\!\!\!-Y^2$$
$$CH_3-CH_2 \diagup \diagdown CH_2-O \diagup \quad Y^1$$

wherein $Y^1$ is an alkyl group and $Y^2$ is selected from the group consisting of sec-butyl and tert-butyl. The phosphite exhibits enhanced stability including hydrolytic and UV stability, and is useful in stabilizing thermoplastic compositions.

11 Claims, No Drawings

NEO-DIOL PHOSPHITES AS POLYMER STABILIZERS

This is a continuation of application Ser. No. 08/307,545 filed on Sep. 16, 1994 now U.S. Pat. No. 5,424,348 which is a continuation of application Ser. No. 08/096,530 filed on Jul. 22, 1993, now abandoned.

BACKGROUND OF THE INVENTION

1. Field of the Invention

The present invention relates to phosphites, and more particularly related to neoalkyl phenyl phosphites.

2. Description of the Related Art

Neoalkyl phenyl phosphites are known, see Dever et al U.S. Pat. No. 3,714,302 which is incorporated herein by reference. Dever et al teaches neoalkyl phenyl phosphites of the formula:

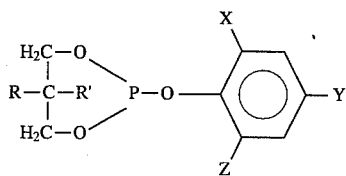

wherein R and R' are independently lower alkyl groups and X, Y and Z are independently selected from the group consisting of —H and alkyl groups of from 1 to 5 carbon atoms, providing that the sum of the carbon atoms in X, Y and Z does not exceed 5, may be simply and economically produced by the reaction of a neoglycol with $PCl_3$ in the absence of a catalyst, HCl acceptor and solvent to produce a crude product of the formula:

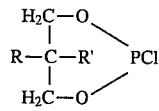

wherein R and R' are defined above, followed by reaction with phenol or a compound of the formula:

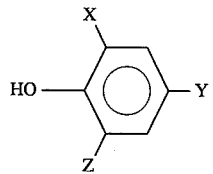

in which X, Y and Z are defined above. The desired product of Dever et al. may be recovered by distillation.

Suitable glycols are listed and include 2-ethyl-2-butyl-1,3 propane diol among others.

Dever et al. U.S. Pat. No. 3,714,302 clearly teaches away from compounds wherein X and Z are both alkyl groups such that they create stearic hinderance. Specifically note col. 3, lines 63 to 65 thereof wherein it states that the proviso that the sum of X, Y and Z does not exceed 5 excludes such phenols as 2,6-di-tertiarybutyl phenols from consideration because of stearic hinderance problems.

Dever et al U.S. Pat. No. 3,467,733 discloses compounds of the formula:

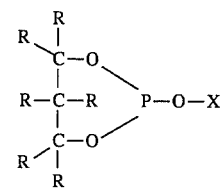

wherein R is independently selected from the group consisting of hydrogen, alkyl of 1 to 6 carbon atoms, and halogen; X is a monovalent radical of the formula:

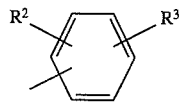

wherein $R^2$ independently selected from the group consisting of hydrogen, alkyl of 1 to 12 carbon atoms and halogen, and $R^3$ is independently selected from the group consisting of alkyl of 1 to 12 carbon atoms and halogen, and sets forth in claim 7 a phosphite of the formula:

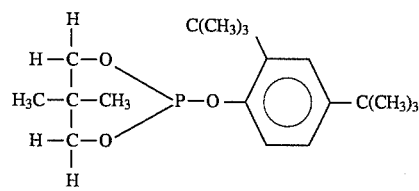

Many of these phosphites can, however, experience thermal stability problems, hydrolytic stability problems, and/or ultraviolet light discoloration problems.

Consequently, there is a need for a neoalkyl aryl phosphite exhibiting improved ultraviolet and hydrolytic stability.

SUMMARY OF THE INVENTION

The present invention involves a neoalkyl aryl phosphite of the formula:

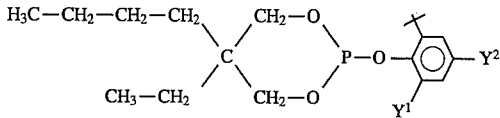

wherein $Y^1$ is independently selected from the group consisting of alkyl radicals, and preferably $Y^1$ is a tert-butyl group and $Y^2$ is a tert-butyl or sec-butyl group. The phosphites are useful to stabilize organic materials against thermal oxidative degradation, exhibit enhanced hydrolytic stability and are resistant to UV yellowing.

DETAILED DESCRIPTION OF THE INVENTION

The phosphite is a compound of the formula:

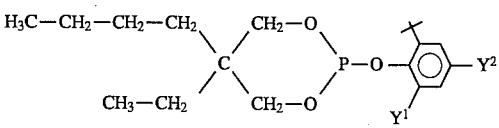

The phosphite may be made by the reaction of 2-ethyl-2-butyl-1,3-propane diol with PCl₃ in the absence of a catalyst, HCl acceptor and solvent to produce an intermediate product of the formula:

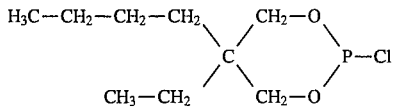

followed by the reaction with a hydroxyaryl compound of the formula:

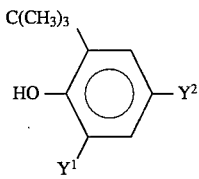

wherein $Y^1$ and $Y^2$ are as defined above. Suitable reaction methods are set out in Great Britain Patent 2087399A, Spivak et al. U.S. Pat. No. 4,318,845 issued 1982, and Article in Phosphourous & Sulfur Journal by J. D. Spivak et al. 1983, vol. 15, pp. 9–13, all of which are incorporated herein by reference.

The reaction between the diol and PCl₃ may be conducted in known manner, as by mixing the reactants together at room temperature, or preferably, by cooling the PCl₃ to a temperature between 5–15 degrees centigrade prior to addition of diol to the reactor. An excess of either reactant may be employed although it is preferred to operate with substantially stoichiometric amounts of the diol and PCl₃. The reaction temperature is preferably maintained between 5–15 degrees centigrade. This temperature may be readily controlled by regulating the rate of diol addition. The esterification reaction is quite exothermic in the absence of a solvent, but a temperature moderating effect is produced by the cooling effect of vigorous HCl evolution. Hence, by effective control of diol addition, the reaction may be made self-regulating in the temperature range between 5–15 degrees centigrade.

After the reaction has gone to completion, the bulk of the by-product HCl may optionally be removed by gently raising the temperature of the product to about 50 degrees centigrade and applying a vacuum.

The reaction between the intermediate product of the reaction discussed in the preceding paragraph and hydroxyaryl compound may be conducted in the same reaction vessel that was employed to produce the crude intermediate by merely introducing the hydroxyaryl compound into the reactor.

The reaction between the hydroxyaryl compound and the intermediate product in some instances may be carried out at a temperature between 35 to 100 degrees centigrade and preferably between about 45 to about 80 degrees centigrade. The pressure of the reaction system is maintained between about 50 millimeters mercury absolute to atmospheric pressure. The reaction reaches substantial completion in from 1 to about 8 hours and for practical purposes it is preferably operated under temperature and pressure conditions which will afford the maximum amount of product within 3 to about 5 hours. Although a stoichiometric excess of either reactant may be employed, it is preferred to operate with substantially stoichiometric quantities.

The hydroxyaryl compound may be any compound of the formula:

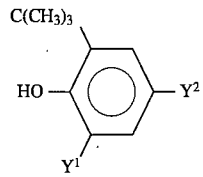

in which $Y^1$ is selected from the group consisting of alkyl groups preferably having from 1 to 8 carbon atoms, more preferably methyl or t-butyl. The reaction can be completed in the presence of a base such as an amine acceptor. Since $Y^1$ is an alkyl group, an amine acceptor should be added to help drive this reaction. If $Y^1$ is a tert-alkyl group, such as t-butyl, then a stociometeric amount of amine acceptor should be present. $Y^2$ is selected from sec-butyl and t-butyl groups. If $Y^2$ is a t-butyl group then the phosphite is a solid at room temperature. Preferably $Y^2$ is sec-butyl so that the phosphite is a liquid at room temperature.

After completion or near completion of the reaction, HCl generated during the process may readily be substantially removed by evacuating the reactor vessel. No special precautions need to be taken to remove all the HCl present, as by addition of HCl acceptor or via controlled neutralization of the acidity. The product may then be recovered by distillation, or crystallization.

The phosphites have $Y^1$ as an alkyl group such as methyl or t-butyl in order to inhibit ultraviolet light yellowing of the phosphite. If $Y^1$ is hydrogen the phosphite will have sensitivity to UV yellowing. The preferred phosphite has a phenolic degradation product boiling point of greater than 250° C., more preferably greater than 260° C. so that the volatility of the degradation product during processing of the stabilized polymer, such as polyolefins such as polypropylene which processes at 240° C. and above, is minimized. The problem of excessive volatiles can be minimized by employing an 2,4-di-butyl-6-alkyl phenyl group because such groups have corresponding 2,4-di-butyl-6-alkyl phenol degradation products which have a boiling point of greater than 260° C.

The present invention also is a stabilized polymer composition which includes an effective amount of one or more of the phosphites described above. An amount of the phosphites of the invention is considered to be an "effective amount" when the polymer composition containing the phosphites of the invention shows improved stability in any of its physical or color properties in comparison to an analogous polymer composition which does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, although most compositions will contain about 0.025 phr or more. The polymer composition may be thermoset in nature including unsatured polyesters, phenolics, epoxie, urethanes, coating resins and crosslinkable latexes.

The polymer may also be any thermoplastic known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinyl chloride/ABS or other impact modified polymers, such as methacrylonitrile and alphamethylstyrene containing ABS, and polyester/ABS or polycarbonate/ABS and polyester plus some other impact modifier may also be used. Such polymers are available commercially or may be made by means well known in the art. However, the phosphites of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidenenorbornene; as well as mixtures of such copolymers and their mixtures with polymers mentioned above, for example polypropylene/ethylene propylene-copolymers, LDPE/EVA, LDPE/EAA, LLDPE/EVA and LLDPE/EAA.

Thermoplastic polymers may also include styrenic polymers, such as polystyrene, poly-(p-methylstyrene), poly-(α-methylstyrene), copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethylacrylate/styrene/acrylonit rile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/-butadiene/styrene, styrene/isoprene/styrene, styrene/ethylene/butylene/styrene or styrene/ethylene/propoylene styrene. Styrenic polymers may additionally or alternatively include graft copolymers of styrene or alphamethylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/-propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs, such as polymethacrylonitrile, polyacrylonitrile, acrylonitrile/-butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymers, vinyl chlorideethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate tercopolymer, vinyl chloride-acrylic acid ester copolymers, vinyl chloridemaleic acid ester copolymers, vinyl chloride-methacrylic acid ester copolymers, vinyl chloride-acrylonitrile copolymer and internally plasticized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2(2,2,4(4-hydroxyphenyl)propane) terphthalate and polyhydroxybenzoates as well as block-copolyetheresters derived from polyethers having hydroxyl end groups.

Polyamides and copolyamides which are derived from diamines and dicarboxylic acids and/or from aminocarboxylic acids or the corresponding lactams, such as polyamide, 4,polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The resulting stabilized polymer compositions of the invention may optionally also contain various conventional additives, such as the following:

1. Antioxidants 1.1 Alkylated monophenols, for example: 2,6-di-tertbutyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(alphamethylcyclohexyl)- 4,6 dimethylphenol, 2,6-dioctadecyl-4-methylphenol, 2,4,6,-tricyclohexyphenol, 2,6-di-tert-butyl-4-methoxymethylphenol.

1.2 Alkylated hydroquinones, for example, 2,6-di-tert-butyl-4-methoxyphenol, 2,5-di-tert-butyl-hydroquinone, 2,5-di-tert-amylhydroquinone, 2,6-diphenyl-4-octadecyloxyphenol.

1.3 Hydroxylated thiodiphenyl others, for example, 2,2'-thio-bis-(6-tert-butyl-4-methylphenol), 2,2'-thio-bis-(4-octylphenol), 4,4'thio-bis-(6-tert-butyl-3-methylphenol), 4,4'-thio-bis-(6-tert-butyl-2-methylphenol).

1.4 Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(alphamethylcyclohexyl(phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(alphamethylbenzyl)-4-nonylphenol), 2,2'-methylene-bis-(6-(alpha,alpha-dimethylbenzyl)-4-nonyl-phenol). 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane. 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4 -hydroxy-5-methylphenyl)-dicyclopentadiene, di-(2-(3'-tert-butyl-2'hydroxy-5'methyl-benzyl)-6-tert-butyl-4-methylphenyl)terephthalate.

1.5 Benzyl compounds, for example, 1,3,5-tris-(3,5-di-tert-butyl-4-hydroxybenzyl))-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiolterephthalate. 1,3,5-tris-(3,5-di-tert-butyl-4-hydroxybenzyl)isocyanurate. 1,3,5-tris-(4-tert-butyl-3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris-(3,5-dicyclohexyl-4-hydroxybenzyl)isocyanurate.

1.6 Acylaminophenols, for example, 4-hydroxy-lauric acid anilide, 4-hydroxy-stearic acid amilide, 2,4-bis-octylmercapto-6-(3,5-tert-butyl-4-hydroxyanilino)-s-triazine, octyl-N-(3,5-di-tert-butyl-4-hydroxyphenyl)-carbamate.

1.7 Esters of beta-(3,5-di-tert-butyl-4-hydroxyphenol)-propionic acid with nonohydric or polyhydric alcohols, for example, methanol, diethyleneglycol, octadecanol, triethyleneglycol, 1,6-hexanediol, penta-erythritol, neopentylglycol, tris-hydroxyethyl isocyanurate, thiodiethyleneglycol, di-hydroxyethyl oxalic acid diamide.

1.8 Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

1.9 Esters of beta-(5-tert-butyl-4-hydroxy-3-methylphenyl) propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4-hydroxyphenol)-propionic acid for example, N,N'-di-(3,5-di-tert-butyl-4-hydroxyphenylpropionyl)-hexamethylen-diamine, N,N'-di-(3,5-di-tert-butyl-4-hydroxyphenylpropionyl)trimethylenediamine, N,N'-di-(3,5-di-tert-butyl-4-hydroxyphenylpropionyl)-hydrazine.

2. UV absorbers and light stabilizers.

2.1 2-(2'-hydroxyphenyl)-benzotriazoles, for example, the 5'methyl-,3'5'-di-tert-butyl-,5'-tert-butyl-,5'(1,1,3,3-tetramethylbutyl)-,5-chloro-3',5'-di-tert-butyl-,5-chloro-3'tert-butyl-5'methyl-,3'sec-butyl-5'tert-butyl-,4'-octoxy,3',5'-di-tert-amyl-3',5'-bis-(alpha, alphadimethylbenzyl)-derivatives.

2.2 2-Hydroxy-benzophenones, for example, the 4-hydroxy-4-methoxy-,4-octoxy,4-decloxy-,4-dodecyloxy-,4-benzyloxy,4,2',4'-trihydroxy-and 2'hydroxy-4,4'-dimethoxy derivative.

2.3 Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butyl-phenyl-3,5-di-tert-butyl-4-hydroxybenzoate and hexadecyl-3,5-di-tert-butyl-4-hydroxybenzoate.

2.4 Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

2.5 Nickel compounds, for example, nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

2.6 Sterically hindered amines, for example bis(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6,-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperdine; and N-(1-hydroxy-2,2,6,6-tetramethyl-piperidin-4-71)-epsiloncaprolactam.

2.7 Oxalic acid diamides, for examples, 4,4'-dioctyloxyoxanilide, 2,2'-di-octyloxy-5',5'-di-tert-butyloxanilide, 2,2'-di-dodecyloxy-5',5'di-tert-butyl-oxanilide, 2-ethoxy-2'-ethyloxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of ortho-and para-methoxy-as well as of o-and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzylidenoxalic acid dihydrazide.

4. Phosphites and phosphonites, for example, triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2, 4-di-tert-butylphenyl)phosphite, diisodecyl pentaerythritol diphosphite, bis(2,4-di-tert-butylphenyl)pentaerythritol diphosphite tristearyl sorbitol triphosphite, and tetrakis(2,4-di-tert-butylphenyl)4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palpitate, antimony pyrocatecholate or zinc pyrocatecholate.

8. Nucleating agents, for example, 4-tert butylbenzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-(N, N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

11. Other additives, for example, plasticizers, lubricants, emulsifiers, pigments, optical brighteners, flameproofing agents, anti-static agents, blowing agents and thiosynergists such as dilaurythiodipropionate or distearylthiodipropionate.

Polymeric particles may be coated with the present phosphites alone or in combination with other stabilizers for stabilization of the polymeric material. Particles may be spherical in shape and may be made by processes such as "Reactor Granule Technology" as disclosed in P. Galli and J. C. Halock, The Reactor Granule—A Unique Technology for the Production of a New Generation of Polymer Blends, Society of Plastics Engineers, Polyolefin III International Conference Feb. 24–27, 1991 and as disclosed in Pedrazzeth et al. U.S. Pat. No. 4,708,979 entitled Process for the Stabilization of Spherically Polymerized Polyolefins issued Nov. 24, 1987 both of which are disclosed herein by reference. Particle formation may be achieved by support Ziegler-Natta Catalyst systems. Suitable commercial processes are known by the trademarks: Spheripol, Addipol and Spherilene.

Olefin polymers may be produced by polymerization of olefins in the presence of Ziegler-Natta catalysts optionally on supports such as but not limited to Mg $Cl_2$, chronium salts and complexes thereof, optionaly supported on Silica or other materials. They may also be produced utilizing catalysts based on cyclopentadiene complexes of metals typically complexes of Ti and Zr.

Consistent with the invention, the phosphites of the invention may be added to the polymer at any time prior to or during fabrication into articles and may be combined with the polymer by any of a variety of means known in the art, such as by preblending or by being fed directly into fabrication equipment.

The following examples illustrate the present invention.

EXAMPLES

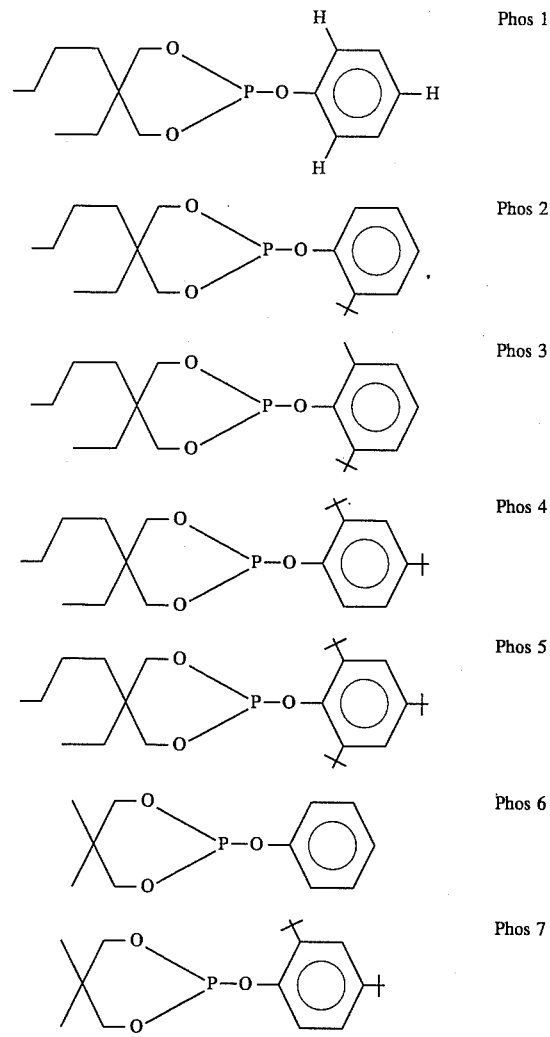

The Examples set out the half-life of phosphites in films pressed from a polypropylene resin composition containing 1% by weight of the respective phosphite. Half-life was measured at the time to ½ depletion of the initial phosphite loading upon exposure of the film to a temperature of 60° C. and a nominal relative humidity of 75%. It is believed that degradation of the phosphite in the film was due primarily to hydrolysis of the phosphite. Phos 5 illustrates the phosphites of the present invention and their results are shown in example 1. Examples A, B, C, D, E & F are comparative examples. The additive is compounded into polymer at 5000–10000 ppm, and the initial color recorded. The polymer sample is then exposed to short wave UV light (as the 254 mm light from a Mineralite™ Lamp. Model UVGL-5) for a set time interval (usually 10 min.) at a set distance from the light source (usually less than 1 inch). The color of the polymer sample is recorded and the change in yellowness index (delta YI) is calculated. Samples that fail the UV yellowing test will have a delta YI>5, typically in the 20–40 range. Samples that pass the UV yellowing test will have delta YI<5, typically in the 0–2 range.

TABLE I

| Example | Phos Type | t ½ (days) | U.V. Yellowing |
|---|---|---|---|
| A | Phos 1 | 4 | No |
| B | Phos 2 | 15 | Yes |
| C | Phos 3 | 21 | No |
| D | Phos 4 | 22 | Yes |
| 1 | Phos 5 | 37 | No |
| E | Phos 6 | <2 | No |
| F | Phos 7 | 12 | Yes |

Note the greater hydrolytic stability of the phosphite of Example 1 over the comparative phosphites. Also note the resistance of Example 1 to U.V. yellowing. Table II illustrates the high boiling point of the 2,4,6-tri-t-butyl phenol of Example 1. The data herein demonstrates the improved properties and combination of properties of the phosphite of Example 1. The diol of the phosphite of Example 1 provides enhanced hydrolytic stability over the lower molecular weight diols of Phos 6 and Phos 7 (compare Phos 4 with Phos 7).

TABLE II

| Phenolic | Boiling point |
|---|---|
|  | 230° C. |
|  | 235° C. |
|  | 237° C. |
|  | 263° C. |
|  | 269° C. |

TABLE II-continued

| Phenolic | Boiling point |
|---|---|
|  | 278° C. |

I claim:

1. A phosphite of the formula:

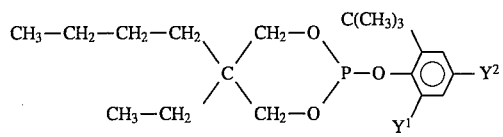

wherein $Y^1$ is alkyl and $Y^2$ is selected from the group consisting of t-butyl and sec-butyl.

2. The phosphite of claim 1 wherein $Y^1$ is methyl.

3. The phosphite of claim 1 wherein $Y^1$ is a tert-butyl group.

4. A thermoplastic polymeric composition comprising a thermoplastic resin and from 0.01 to 1.0 percent by weight of a phosphite as claimed in claim 1 based on the total weight of the composition.

5. A thermoplastic polymeric composition comprising a thermoplastic resin and from 0.01 to 1.0 percent by weight of a phosphite as claimed in claim 2 based on the total weight of the composition.

6. A thermoplastic polymeric composition comprising a thermoplastic resin and from 0.01 to 1.0 percent by weight of a phosphite as claimed in claim 3 based on the total weight of the composition.

7. A thermoplastic composition as claimed in claim 4 wherein said thermoplastic resin is selected from the group consisting of polyolefins, polycarbonates, polyesters, polyvinyl chloride and polystyrenes.

8. A thermoplastic composition as claimed in claim 4 wherein said thermoplastic resin is polypropylene.

9. A thermoplastic composition as claimed in claim 4 wherein said composition consists essentially of said thermoplastic resin and said phosphite.

10. A thermoplastic composition as claimed in claim 9 wherein said $Y^1$ is a tert-butyl group.

11. The composition of claim 9 wherein said $Y^1$ is a methyl group.

* * * * *